US00PP24584P2

(12) United States Plant Patent
Zampini

(10) Patent No.: US PP24,584 P2
(45) Date of Patent: Jul. 1, 2014

(54) ***LONICERA* PLANT NAMED 'LOGOZAM'**

(50) Latin Name: *Lonicera maackii*
Varietal Denomination: Logozam

(71) Applicant: James W. Zampini, Madison, OH (US)

(72) Inventor: James W. Zampini, Madison, OH (US)

(73) Assignee: Lake Country Nursery, Perry, OH (US)

( * ) Notice: Subject to any disclaimer, the term of this patent is extended or adjusted under 35 U.S.C. 154(b) by 0 days.

(21) Appl. No.: 13/986,001

(22) Filed: Mar. 21, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

U.S. PATENT DOCUMENTS

PP16,240 P3 * 2/2006 Edmonds et al. ..... Plt./226
PP20,939 P2 * 4/2010 Gessell ..... Plt./226

OTHER PUBLICATIONS

Upshoot Plant List Use Catalog (retrieved from the internet on Sep. 24, 2013 at <http://www.upshoothort.com/wp-content/uploads/2012/03/UpShoot-Plant-List-Use-Binder2.pdf>, 1 page).*

* cited by examiner

*Primary Examiner* — June Hwu
*Assistant Examiner* — Keith Robinson
(74) *Attorney, Agent, or Firm* — Penny J. Aguirre

(57) ABSTRACT

A new cultivar of *Lonicera*, 'Logozam', characterized by its large bright yellow fragrant flowers, its upright and rounded plant habit, its red fruit, its dark green foliage, and its vigorous growth habit.

1 Drawing Sheet

Botanical classification: *Lonicera maackii.*
Variety denomination: 'Logozam'.

BACKGROUND OF THE INVENTION

The present invention relates to a new and distinct cultivar of *Lonicera maackii*, and will be referred to hereafter by its cultivar name, 'Logozam'. 'Logozam' is a new cultivar of amur honeysuckle, a shrub grown for use as an ornamental landscape plant.

The Inventor discovered the new cultivar as naturally occurring whole plant mutation in a seedbed at his nursery in Perry, Ohio in 2009. The seedbed had been planted with seeds from an unnamed plant of *Lonicera maackii.*

Asexual propagation of the new cultivar was first accomplished by the Inventor using stem cuttings in summer of 2009 in Perry, Ohio. Asexual propagation of the new cultivar by stem cuttings has been determined that the characteristics are stable and are reproduced true to type in successive generations.

SUMMARY OF THE INVENTION

The following traits have been repeatedly observed and represent the characteristics of the new cultivar as grown outdoors in a trial plot in Perry, Ohio. These attributes in combination distinguish 'Logozam' as unique cultivar of *Lonicera.*

1. 'Logozam' exhibits large bright yellow fragrant flowers.
2. 'Logozam' exhibits an upright and rounded plant habit.
3. 'Logozam' exhibits red fruit.
4. 'Logozam' exhibits dark green foliage.
5. 'Logozam' exhibits a vigorous growth habit.

The parent plant of 'Logozam' differs from 'Logozam' in having flowers that are smaller in size and lighter yellow in color and in having a more spreading and less rounded plant habit. The only cultivar of *Lonicera maakii* known to the Inventor is 'Rem Red' (not patented). 'Rem Red' is a seed strain that is similar to the species in plant habit but with more profuse seed production and increased disease resistance. 'Rem Red' differs from 'Logozam' in having a more spreading plant habit and in having smaller, lighter yellow flowers. 'Logozam' can be compared to the cultivar 'Scentsation' (U.S. Plant Pat. No. 16,240). 'Scentsation' differs from 'Logozam' in being a cultivar of *Lonicera periclymenum*, a species with a vining plant habit, whereas 'Logozam' is a cultivar of *Lonicera macckii*, a species that is a shrub with an upright plant habit. 'Scentsation' differs further from 'Logozam' in having flowers that are borne in whorls on the terminal of the stems, whereas the flowers of 'Logozam' are borne in pairs at the axillary nodes of the stems, and in having foliage that is blue-green on the lower surface with acute to obtuse apices.

BRIEF DESCRIPTION OF THE DRAWING

The accompanying colored photograph was taken in mid summer and illustrate the overall appearance and distinct characteristics of a 4 year-old plant the new *Lonicera* as grown in a trial garden in Perry, Ohio. The photograph in FIG. 1 provides an overall view of 'Logozam' in bloom. The colors in the photograph may differ slightly from the color values cited in the detailed botanical description, which accurately describe the colors of the new *Lonicera.*

DETAILED BOTANICAL DESCRIPTION

The following is a detailed description of 3 year-old plants the new *Lonicera* as grown in 3-gallon containers in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms in early June in Perry, Ohio.

*Plant type.*—Deciduous shrub.

*Plant habit.*—Upright and rounded.

*Plant height and spread.*—Reaches 3.7 to 4.6 m in height and spread.

*Diseases and pests.*—The new cultivar has been observed to be disease free to date under the conditions of trials.

*Cold hardiness.*—At least in U.S.D.A. Zone 4.

*Root description.*—Fibrous.

*Propagation.*—Softwood stem cuttings, under mist in summer.

*Growth rate.*—Vigorous.

Stem description:

*Shape.*—Oval.

*Stem color.*—New growth; 138B, mature wood; 197C, maturing to bark 197A.

*Stem size.*—Main branches; about 1.3 cm in diameter measured 30 cm above the soil level, lateral branches; average of 6.4 mm in diameter and 91 cm in length.

*Stem surface.*—New growth; glabrous and slightly glaucous, mature wood is dull and smooth and becoming bark-like as it ages.

*Internode length.*—7.6 cm.

*Branching.*—Multi-stemmed from base, with new growth emerging in opposite arrangement from axillary nodes.

Foliage description:

*Leaf shape.*—Ovate-elliptic.

*Leaf division.*—Simple.

*Leaf base.*—Broadly cuneate.

*Leaf apex.*—Acuminate.

*Leaf fragrance.*—None.

*Leaf venation.*—Pinnate, slightly conspicuous, color on upper surface, 138A, color on lower surface; 138B.

*Leaf margins.*—Slightly wavy.

*Leaf arrangement.*—Opposite.

*Leaf attachment.*—Petiolate.

*Leaf surface.*—Glabrous on upper surface and lower surface.

*Leaf internode length.*—Average of 7.6 cm.

*Leaf size.*—Average of 6.4 cm in length and 1.9 cm in width.

*Leaf quantity.*—Average of 12 pair per branch 91 cm in length.

*Leaf color.*—Newly expanded leaves upper surface; 141C newly expanded leaves lower surface; 138B, mature leaves upper surface; 141B, mature leaves lower surface; 138A, fall color; leaves are quickly dropped, no distinct coloration.

*Petioles.*—About 3.5 mm in length and 3.5 mm in width, 138A in color, glabrous surface.

*Stipules.*—None.

Inflorescence description:

*Inflorescence type.*—Tubular flowers borne in pairs at axillary nodes on second year growth.

*Inflorescence size.*—An average of 8 cm in length and 12 in diameter.

*Flower buds.*—Oblanceolate in shape, 15B in color, an average of 6 cm in length and 3.8 cm in width.

*Flower fragrance.*—Very fragrant.

*Lastingness of inflorescence.*—Individual flowers lasts about 30 days, self-cleaning.

*Flower quantity.*—Average of 8 flowers per terminal inflorescence.

*Flower type.*—Tubular, 2-lipped.

*Flower size.*—Average of 7.1 cm in diameter and 2.3 cm in depth.

*Peduncles.*—None sessile to stem.

*Pedicels.*—None, sessile to stem.

*Calyx.*—5-starred, inconspicuous, average of 3 mm in diameter and 4 mm in depth.

*Sepals.*—5, un-fused portion in triangular shape, acute apex, fused base, 144A in color, entire margin on tips, glabrous surface.

*Petals.*—5, 4 fused into tube with apex of each free, tube portion is about 3.8 cm in length and __1 cm in width, free portion is 2-lipped with upper lip comprised of 4 petals flared outward to reflexed and lower lip comprised of 1 petal that is slightly reflexed, free portion of fused petals are about 4 cm in length and 1.3 cm in width, together free portion of upper lip petals are triangular in shape and about 2 mm in length and width, free portion of lower lip petal is oblanceolate in shape about 5 cm in length and 1.5 cm in width, all free petals portions have a triangular apex and entire margin, outer and inner surface is glabrous, color of inner and outer surface when opening is 155A, color of inner surface when mature is 15C, color of outer surface when mature is 16D.

Reproductive organs:

*Gynoecium.*—1 pistil, about 2.2 cm in length, style is about 2 cm in length, and 155A in color, stigma is about 2 mm in diameter and depth, flattened globose in shape and 15B in color, ovary is inferior, ovoid in shape, and 144A in color.

*Androcoecium.*—5 stamens, filaments are 155A in color and about 2.2 cm in length, anthers are about 1 cm in length, dorsifixed, 161A in color, pollen was not observed.

*Fruit and seed.*—True berry, round in shape, about 1 cm in diameter, produced in late summer, N34A in color, seed was not observed.

It is claimed:

1. A new and distinct cultivar of *Lonicera* plant named 'Logozam' as herein illustrated and described.

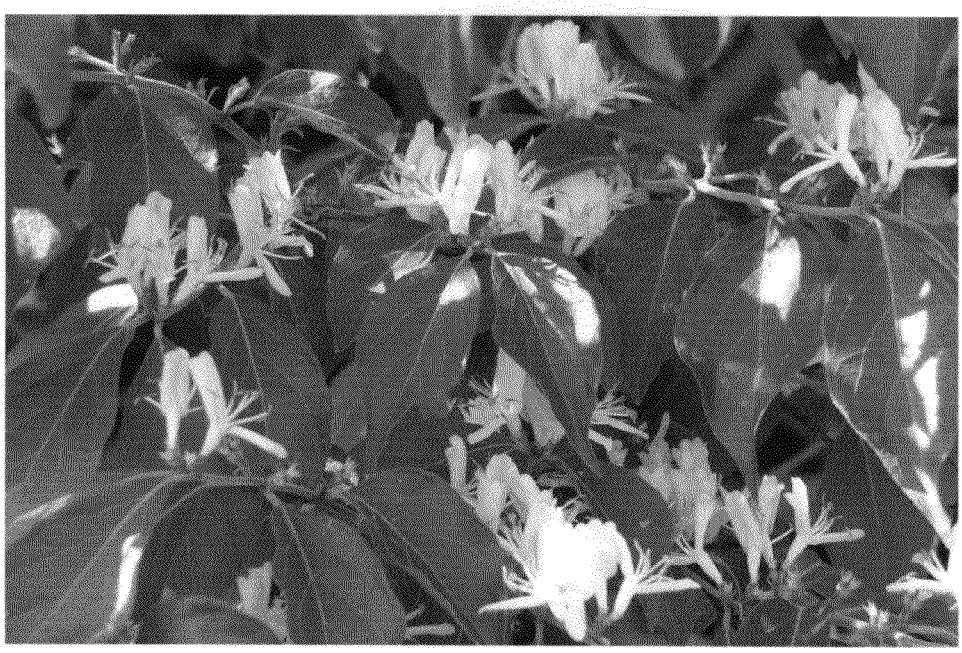

* * * * *